United States Patent [19]

Murtaugh et al.

[11] 4,348,209

[45] Sep. 7, 1982

[54] DETERMINING QUANTITATIVE DEGREE OF ETHYLENE OXIDE EXPOSURE IN STERILIZATION PROCESSES

[75] Inventors: J. Barry Murtaugh, Barrington; Dean G. Laurin, Lake Zurich, both of Ill.; John E. Kling, Dallas, Tex.; Archie G. Woodworth, Barrington, Ill.

[73] Assignee: Baxter Travenol Laboratories, Inc., Deerfield, Ill.

[21] Appl. No.: 305,418

[22] Filed: Sep. 25, 1981

[51] Int. Cl.³ .................. G01N 31/04; G01N 31/10
[52] U.S. Cl. .................. 23/232 R; 55/158; 210/638; 422/61; 422/83; 435/31
[58] Field of Search ............ 23/232 R; 422/57, 58, 422/61, 83, 86, 88; 435/31; 210/638; 55/158, 387; 73/76, 433

[56] References Cited

U.S. PATENT DOCUMENTS

| | | | |
|---|---|---|---|
| 2,998,306 | 8/1961 | Huyck et al. | 23/232 R |
| 3,911,080 | 10/1975 | Mehl et al. | 55/158 |
| 4,015,937 | 4/1977 | Miyamoto et al. | 23/232 R |
| 4,040,805 | 8/1977 | Nelms | 55/158 |
| 4,162,942 | 7/1979 | Gunther | 23/232 R |
| 4,165,633 | 8/1979 | Raisanen | 73/76 |
| 4,266,026 | 5/1981 | Breslau | 210/638 |
| 4,269,804 | 5/1981 | Kring | 55/158 |

Primary Examiner—Michael S. Marcus
Attorney, Agent, or Firm—Paul C. Flattery; John A. Caruso; Garrettson Ellis

[57] ABSTRACT

A method of quantitatively determining the amount of exposure of an object to ethylene oxide gas. A pre-weighed ethylene oxide-permeable container, which encloses a predetermined amount of catalyst for the reaction of the ethylene oxide gas to form a liquid, is placed adjacent to the object. The object and container are then exposed to ethylene oxide gas for controlled time and at a known humidity and temperature. The container is then reweighed. The weight gain of the container is a quantitative indication of the amount of exposure to ethylene oxide gas. The test system may be calibrated against its effect in known concentrations of ethylene oxide gas, so that the precise amount of exposure to ethylene oxide gas can be determined.

15 Claims, 1 Drawing Figure

DETERMINING QUANTITATIVE DEGREE OF ETHYLENE OXIDE EXPOSURE IN STERILIZATION PROCESSES

TECHNICAL FIELD AND DESCRIPTION OF PRIOR ART

Many medical devices such as parenteral solution or blood administration sets, hemodialyzers, packaged bandages, and the like are sterilized after packaging by exposure to ethylene oxide gas. After such exposure to the ethylene oxide gas, the packaged contents, which includes a porous window which permits the ethylene oxide gas to pass into and out of the package, remains sterile until the package is opened. Many large medical supply companies use this sterilizing technique.

One continuing problem of all sterilization techniques is that it is desirable to have a double-check means to determine that the sterilizing conditions were actually applied to the item desired to be sterilized. Human error and mechanical breakdown can, of course, occasionally result in a failure in which, inadvertently, sterilizing conditions are not achieved. For example, for a number of reasons it may be possible that an insufficient amount of ethylene oxide gas is charged into the sterilizing chamber during a commercial sterilizing process. An obstruction may develop in the ethylene oxide line, or the operator may be negligent or inattentive. Similarly, due to some special circumstance, the ethylene oxide may fail to distribute properly through the sterilizer so that a few packaged items in one isolated area do not achieve adequate sterilizing exposure to ethylene oxide.

For this reason, indicator devices for determining the presence of sterilizing conditions are commercially available. Some of the devices are responsive to the presence of ethylene oxide gas, for example Steri-dot® indicator of the Propper Mfg. Company, which gives a color indication. Other devices indicate the effect of steam or heat sterilization.

However, to date, there has been no indicator which provides a simple system for positively determining overall exposure to ethylene oxide gas which provides an effectively quantitative determination, if desired, of the amount of exposure to ethylene oxide gas, which is a function of the ethylene oxide concentration and the time of exposure.

By this invention, a quantitative determination of overall exposure to ethylene oxide gas can be obtained, so that positive and direct confirmation of the application of a sterilizing ethylene oxide exposure can be confirmed by this invention. The invention of this application is very inexpensive and easy to handle, and the cartridges used herein for the determination of ethylene oxide exposure are reusable over usually several ethylene oxide exposures, for cost savings.

DESCRIPTION OF THE INVENTION

In accordance with this invention, a method is provided for quantitatively determining the amount of exposure of an object to ethylene oxide gas. A preweighed ethylene oxide-permeable container which encloses a predetermined amount of catalyst for the reaction of ethylene oxide to form a liquid is placed adjacent to the object to be tested. The container is impermeable to the liquid formed and the catalyst. If desired, the ethylene oxide-permeable container may be placed within the object for a determination of ethylene oxide penetration for the object to be tested. This is considered to be within the scope of the term "adjacent".

Following this, the object and the container may be exposed to ethylene oxide gas for a controlled period of time and under conditions of known temperature. Typically, some water vapor is present.

The container can then be reweighed, the resulting weight gain of the container being a quantitative indication of the amount of exposure to ethylene oxide gas. This weight gain can be rendered more quantitative and meaningful in the light of calibration tests for the specific ethylene oxide gas exposure system being utilized, so that the effect of small variations in time, humidity, and temperature on the weight gain in the specific system may be predetermined.

Accordingly, the overall exposure of the container to ethylene oxide gas can thus be known on a quantitative basis. In a commercial sterilization system, failure of the container to achieve a required minimum weight gain would be an indication that a failure in the system has taken place, and that the sterilization process may not have been effective.

A typical reaction that is used to form a liquid from ethylene oxide gas is the acid-catalyzed hydrolysis reaction of ethylene oxide. Initially, in the presence of an acid catalyst, the ethylene oxide reacts to form ethylene glycol with water vapor, or with a proton from the acid catalyst. Following this, the resulting product may polymerize into a polyglycol, with the result that a liquid is formed adjacent the catalyst.

The container which encloses the catalyst, as stated above, has at least a window or the like in it which is permeable to the ethylene oxide, but is impermeable to liquid formed at the catalyst. Accordingly, the container traps the glycol and polyglycol liquid as it is formed, resulting in a weight gain of the container which can be measured.

Accordingly, the preweighed container may be exposed to the ethylene oxide gas. Differences in humidity and temperature effect the rate of reaction, while, of course, differences in the type and grade of catalyst will also affect the reaction rate. However, these can be easily controlled, with small deviations being calibrated by prior testing, to result in a quantitative indication of exposure of an object to ethylene oxide gas, which quantitative indication is a function of both concentration of ethylene oxide gas and the period of time of exposure to the gas.

After the ethylene oxide exposure, the container is simply reweighed, with the weight gain representing the desired data.

The containers of this invention are reusable since, upon a second, third, or fourth exposure to ethylene oxide gas, they may continue to gain weight as ethylene oxide gas is consumed with the resumed glycol polymerization reaction. Accordingly, as long as the latest weight data for the container is recorded, so that the weight increase can be determined, it remains effective for at least several exposures to ethylene oxide, as long as the container does not become excessively filled with reaction product so as to seriously interfere with the rate of the reaction.

Numerous catalysts for the hydrolysis and polymerization of ethylene oxide gas are well known. Basically, any acid or base will initiate the reaction, particularly in the presence of water. The presence of water tends to accelerate the reaction, but the reaction will proceed with the creation of higher polyglycols, rather than ethylene glycol and lower polymers, in the presence of only small traces of water vapor or merely adsorbed water or equivalent on the catalyst.

Tungsten, for example, forms an acidic oxide film which permits it to catalyze the reaction. Other acidic oxides may be used. It is, of course, preferable for the catalyst to be in the solid or liquid phase, preferably the solid phase. Of course the catalyst must be impermeably retained in the container along with the glycol liquids formed from ethylene oxide by the reaction.

Preferably, ion exchange resins such as acidic and basic resins of known types are used as the catalyst in this invention. Most preferably, strongly acidic ion exchange resins are used, for example the sulphanated polystyrene type resins sold, for example, by the Rohm and Haas Company under the trademark AMBERLYST. Alternatively acid clays which carry acidic hydrogen may be used, and other polymers and resins having pendant acid groups.

The container utilized herein may be of any desired design where the ethylene oxide gas is permeable to its interior but the catalyst and the liquid reaction product is retained. Specifically, the ethylene oxide-permeable container may be a tube of no more than six inches in length containing the catalyst and sealed at at least one end with a porous, gas-permeable seal. However, various porous envelopes or catalysts encapsulated with ethylene oxide permeable materials may be used as the permeable container of this invention as may be desired.

Typically less than one gram of the catalyst is required for use in each cartridge, down to a practical lower limit of about 50 milligrams, although if accuracy considerations are not high, less may be used. The reaction of course proceeds more slowly when less catalyst is present, and thus the weight gain over a particular period of time will be less when only minute amounts of catalyst are present.

Typically no more than 100 grams of the catalyst would be used in any container, since the reaction of ethylene oxide to form glycols is exothermic, and significant temperature problems could be encountered if excessive amounts of catalyst were used.

DESCRIPTION OF SPECIFIC EMBODIMENTS

Figure 1:
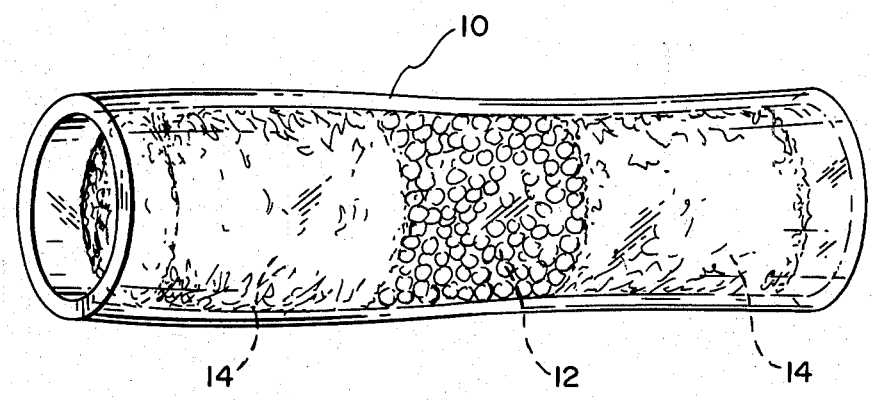
FIG. 1 is a plan view of a preweighed, ethylene oxide permeable container which may be used in accordance with this invention.

Referring to FIG. 1, a polyvinylchloride plastic tube 10 is shown containing about 100 milligrams of sulphonated polystyrene beads 12 sold as a cation exchange resin, for example AMBERLYST XN-1010, sold by the Rohm and Haas Company as stated above. The beads are made of cross-linked polystyrene and are strongly acidic because of the sulphonic acid groups present. The catalyst has a bead size normally of 16 to 50 mesh, a porosity of 41 percent, a surface area of 450 square meters per gram, and a mean pore diameter of 50 angstrom units. The cation exchange capacity is 3.5 mEq/gram.

The catalyst 12 should generally be loosely packed, since it tends to swell in contact with moisture, and also to make room for the glycol liquids to be formed during the process. Plastic tube 10 is typically about 1½ inches long and has an inner diameter of 0.187 inch.

The catalyst beads 12 are enclosed between a pair of porous polyethylene plugs 14 (Porex plugs from the Porex Division of Glasrock Company, Fairburn, Georgia) which plugs retain the catalyst 12 and prevent the loss of any glycols formed, but are permeable to ethylene oxide gas.

Alternatively, other ion exchange resin catalysts may be used instead, for example, AMBERLYST A-21, which is a weakly basic ion exchange resin, and serves to catalyze the reaction. Likewise, AMBERLYST 15, another variety of strongly acidic ion exchange resin, may be used.

Tubes 10, of the type shown in FIG. 1, may be utilized to monitor the effectiveness of an ethylene oxide sterilization procedure in a conventional ethylene oxide sterilizing chamber filled with items for sterilization, for example packaged intravenous administration sets or medical procedure trays of a commercial design. The gas fed into the sterilizer may be 12 percent ethylene oxide by weight and 88 percent by weight of a Freon-type gas. Alternatively, 100 percent ethylene oxide may be used.

By way of specific example, a series of tubes 10 each utilizing essentially 100 milligrams of the AMBERLYST XN-1010 catalyst were inserted into sterilizers adapted to receive 12 percent ethylene oxide, 88 percent Freon gas. The experiment was run at two different temperatures, and varying times of exposure to the gas were applied. Each of the containers were individually preweighed so that the weight gain of the containers through the process could be monitored. The results of the various weight gains are indicated in Table I below for the reaction times and temperatures.

TABLE I

| Time of Exposure | Weight Gain (mg./gm. of catalyst) at 105° F. | Weight Gain (mg./gm. of catalyst) at 125° F. |
|---|---|---|
| 30 minutes | 14 ± 5 | 128 ± 4 |
| 60 minutes | 74 ± 5 | 188 ± 26 |
| 120 minutes | 203 ± 5 | 317 ± 13 |
| 240 minutes | 461 ± 13 | 620 ± 15 |

It can be seen that the characteristic and continuous weight gain takes place over the time of exposure to ethylene oxide gas as the reaction inside of tube 10 continues. It can also be seen that the reaction proceeds more rapidly at higher temperature. Accordingly, calibration charts can be made for any given system. The humidity in these cases did not vary enough to significantly affect the results.

Accordingly, it can be seen that the characteristic weight gain behavior of the particular system can be precalibrated so that the sterilization process can be monitored on a routine industrial basis. If, under the conditions of 105° F. in this particular sterilization system and an exposure of 60 minutes, the weight gain turns out to be only 20 milligrams per gram of catalyst, it would be clear that a significant failure had taken place in the system. This failure otherwise might not be determinable by any other means, with the result that unsterilized product might enter into the channels of commerce, but for the use of this invention.

By the method of this application, the overall exposure of ethylene oxide can be determined by reweighing the container as stated above. However, it is also possible to monitor the amount of water present in the sterilization process, typically in the form of relative humidity at the temperature of sterilization.

Relative humidity is a significant parameter of ethylene oxide sterilization. Even if normally adequate amounts of ethylene oxide gas are present, under conditions of low relative humidity the sterilization process may be less effective than expected. Typically, for the most effective ethylene oxide sterilization, the relative humidity should be at least about 30 percent at the sterilizing temperature. Also, the rate of hydrolysis and polymerization of ethylene oxide in the presence of a catalyst is effected by the relative humidity of the reaction environment.

It is also possible in accordance with this invention to monitor the relative humidity of the reaction system by analysis of the types of reaction products formed by the hydrolysis and polymerization of ethylene oxide in the presence of the catalyst used in this invention. The molecular weight of the polymers, which may be a function of their hydroxyl numbers, found in the container of this invention after the sterilization step serves as an indication of the relative humidity. At low relative humidities, the average molecular weight of the resulting ethylene oxide polymers will be higher than in circumstances where the relative humidity is higher, permitting more hydrolysis reaction to take place. At higher impurities, more molecules of hydrolyzed and polymerized ethylene oxide of lower molecular weight are present.

Thus after reweighing of the container to determine the amount of exposure to ethylene oxide gas, the container may be opened if desired, and the liquid contents thereof analyzed for its hydroxyl number. For example, the hydroxyl number may be easily calibrated to the relative humidity in any given sterilization system, so that both variables may be monitored by the method of this invention.

Accordingly, if the humidity is known, the overall ethylene oxide exposure may be easily determined. However even if the relative humidity is not known, it may be monitored by the same invention. Furthermore, by calibration of the method of this invention to a sterilization process which is repeated on a commercial basis, for example, the weight gain alone can serve as an indicator that both the ethylene oxide gas exposure and the relative humidity are within desired parameters.

It may also be desired to make the preweighed container of this invention by placing the catalyst used on a flexible web, for example in the form of a slurry. Following this, the web may be covered and sealed with a permeable, porous material, for example porous polyethylene, so as to form a series of sealed envelopes which may be separated to form the ethylene oxide-permeable container enclosing the predetermined amount of catalyst. This then may be preweighed in the usual manner and used in accordance with this invention, providing a low cost unit of relatively low weight so that the weight gain during use is a larger fraction of the overall weight of the container.

The above has been offered for illustrative purposes only, and is not intended to limit the scope of the invention of this application, which is as defined in the claims below.

That which is claimed is:

1. The method of quantitatively determining the amount of exposure of an object to ethylene oxide gas, which comprises:

placing adjacent to said object a preweighed ethylene oxide-permeable container which encloses a predetermined amount of catalyst for the reaction of ethylene oxide to form a liquid, said container being impermeable to said catalyst and liquid;

exposing said object and container to ethylene oxide gas for a controlled time and at a determined temperature; and reweighing said container, whereby the weight gain of said container is a quantitative indication of the amount of exposure to ethylene oxide gas.

2. The method of claim 1 in which said catalyst is tungsten.

3. The method of claim 1 in which said ethylene oxide-permeable container comprises a tube no more than six inches long containing said catalyst and sealed at at least one end with a porous, gas-permeable seal.

4. The method of claim 1 in which water vapor is present.

5. The method of claim 1 in which said catalyst is a catalyst for the hydrolysis of ethylene oxide to form glycols.

6. The method of claim 1 in which said catalyst is an ion exchange resin selected from the group consisting of acidic and basic resins.

7. The method of claim 6 in which said ion exchange resin is of a strongly acidic type.

8. The method of quantitatively determining the amount of exposure of an object to ethylene oxide gas, which comprises:

placing adjacent to said object a preweighed ethylene oxide-permeable tube containing a predetermined amount of catalyst for the reaction of ethylene oxide to form a liquid, said catalyst comprising an ion exchange resin selected from the group consisting of acidic and basic resins, said tube being sealed at at least one end with a porous, gas permeable seal, said sealed tube being impermeable to said catalyst and liquid formed by said reaction;

exposing said object and container to ethylene oxide gas for a controlled time and at a determined temperature; and reweighing said tube, whereby the weight gain of said container is a quantitative indication of the amount of exposure to ethylene oxide gas.

9. The method of claim 8 in which said catalyst is a catalyst for the hydrolysis of ethylene oxide to form glycols.

10. The method of claim 9 in which the average degree of polymerization of the liquid formed is measured as a quantitative indication of humidity.

11. The device of claim 10 in which said ion exchange resin is of a strongly acidic type.

12. The method of quantitatively determining the amount of exposure of an object to ethylene oxide gas, which comprises:

placing adjacent to said object a preweighed ethylene oxide-permeable container which encloses a predetermined amount of catalyst for the reaction of ethylene oxide to form a liquid, said container being impermeable to said catalyst and liquid;

exposing said object and container to ethylene oxide gas for a controlled time at a determined temperature;

reweighing said container whereby the weight gain of said container is a quantitative indication of the amount of exposure to ethylene oxide gas; and analyzing the liquid formed to determine its average degree of polymerization, whereby said average degree of polymerization is a quantitative indication of the relative humidity.

13. The method of claim 12 in which said catalyst is an ion exchange resin selected from the group consisting of acidic and basic resins.

14. The method of claim 13 in which said ion exchange resin is of the strongly acidic type.

15. The method of claim 14 in which said liquid formed is analyzed by determination of its hydroxyl number.

* * * * *